(12) United States Patent
Schütze et al.

(10) Patent No.: US 11,371,941 B2
(45) Date of Patent: Jun. 28, 2022

(54) DEVICE AND METHOD FOR THE DETERMINATION OF TRANSFECTION

(71) Applicant: CellTool GmbH, Bernried (DE)

(72) Inventors: Karin Schütze, Tutzing (DE); Raimund Schütze, Tutzing (DE)

(73) Assignee: CellTool GmbH

( * ) Notice: Subject to any disclaimer, the term of this patent is extended or adjusted under 35 U.S.C. 154(b) by 534 days.

(21) Appl. No.: 16/315,010

(22) PCT Filed: Jul. 4, 2017

(86) PCT No.: PCT/EP2017/066698
§ 371 (c)(1),
(2) Date: Jan. 3, 2019

(87) PCT Pub. No.: WO2018/007415
PCT Pub. Date: Jan. 11, 2018

(65) Prior Publication Data
US 2019/0226994 A1  Jul. 25, 2019

(30) Foreign Application Priority Data
Jul. 4, 2016  (DE) ............... 10 2016 212 103.0

(51) Int. Cl.
G01N 21/65 (2006.01)
C12N 15/87 (2006.01)
G01N 21/64 (2006.01)
G01N 33/50 (2006.01)

(52) U.S. Cl.
CPC ............ G01N 21/65 (2013.01); C12N 15/87 (2013.01); G01N 21/6428 (2013.01); G01N 21/6458 (2013.01); G01N 33/50 (2013.01); G01N 2021/6439 (2013.01); G01N 2201/129 (2013.01)

(58) Field of Classification Search
CPC .... G01N 33/50; G01N 21/65; G01N 21/6428; G01N 21/6458
See application file for complete search history.

(56) References Cited

U.S. PATENT DOCUMENTS

| | | | |
|---|---|---|---|
| 2006/0250613 A1 | 11/2006 | Demuth et al. | |
| 2010/0034743 A1 | 2/2010 | Cohen et al. | |
| 2010/0315628 A1 | 12/2010 | Mertsching et al. | |
| 2011/0122407 A1 | 5/2011 | Jalali et al. | |
| 2013/0171685 A1 | 7/2013 | Schutze | |
| 2015/0044751 A1* | 2/2015 | Chiou | C12M 41/00 435/173.6 |
| 2015/0191763 A1* | 7/2015 | Van Nieuwenhze | C07K 9/003 435/32 |
| 2016/0061808 A1 | 3/2016 | Cheung et al. | |
| 2016/0202222 A1 | 7/2016 | Roberts et al. | |
| 2017/0020460 A1 | 1/2017 | Leblond et al. | |

FOREIGN PATENT DOCUMENTS

| | | |
|---|---|---|
| DE | 102006053540 B3 | 1/2008 |
| DE | 102010023099 B3 | 11/2011 |
| KR | 1020120078098 A | 7/2012 |
| WO | 2012158631 A2 | 11/2012 |
| WO | 2014129970 A1 | 8/2014 |

OTHER PUBLICATIONS

Notingher, Ioan, et al. "In situ non-invasive spectral discrimination between bone cell phenotypes used in tissue engineering." Journal of Cellular Biochemistry 92.6 (2004): 1180-1192. (Year: 2004).*
Biedermann et al., "Tissue Engineering of Skin for Wound Coverage", Eur J Pediatr Surg, 2013, pp. 375-382, vol. 23.
Celltool, "BioRam-Photonic fingerprinting", Nov. 2011, http://celltool.de/files/celltool-bioram-flyer_en.pdf.
Charwat et al., "Potential and limitations of microscopy and Raman spectroscopy for live-cell analysis of 3D cell cultures", Journal of Biotechnology, 2015, pp. 29-31, vol. 205.
Eilers, "A Perfect Smoother", Anal. Chem., 2003, pp. 3631-3636, vol. 75:14.
Haber et al., "Ultra-sound-Mediated Mesenchymal Stem Cells Transfection as a Targeted Cancer Therapy Platform", Scientific Reports, 2017, pp. 1-34, vol. 7, Article 42046.
Hammes, "Spectroscopy for the Biological Sciences", 2005, pp. 1-158, John Wiley & Sons, Inc.

(Continued)

*Primary Examiner* — Dominic J Bologna
(74) *Attorney, Agent, or Firm* — The Webb Law Firm

(57) ABSTRACT

The present invention relates to an in vitro method for determining the transfection of a cell or group of cells, wherein said determination is performed spectroscopically. The determination comprises recording at least one Raman spectrum by means of Raman spectroscopy of the cell or group of cells. Furthermore, the present invention relates to a device for determining the transfection of a cell or group of cells, wherein the device comprises as a first unit (i) a microscope system in order to visualize the cells, as a second unit (ii) a Raman spectroscopy system in order to record a Raman spectrum of a cell or group of cells, and as a third unit (iii) an evaluation module which is coupled to the Raman spectroscopy system and which is configured to determine by means of the recorded Raman spectrum whether a cell or group of cells has been transfected.

21 Claims, 7 Drawing Sheets

(56) References Cited

OTHER PUBLICATIONS

Inoue et al., "An impulse to the brain—using in vivo electroporation", Nature Neuroscience Supplement, 2001, pp. 1156-1158, vol. 4.

Ito et al., "Analysis of the surface structure of DNA/polycation/hyaluronic acid ternary complex by Raman microscopy", Journal of Pharmaceutical and Biomedical Analysis, 2010, pp. 268-272, vol. 51.

Jones et al., "SciPy: Open Source Scientific Tools for Python", 2011, http://www.scipy.org/.

Keith et al., "Use of Flow Cytometry to Rapidly Optimize the Transfection of Animal Cells", BioTechniques, 2000, pp. 148-154, vol. 28.

Kim et al., "Mammalian cell transfection: the present and the future", Anal Bioanal Chem, 2010, pp. 3173-3178, vol. 397.

Marino et al., "Bioengineering Dermo-Epidermal Skin Grafts with Blood and Lymphatic Capillaries", Sci Transl Med., 2014, pp. 1-12, vol. 6:221.

Notingher et al., "In Situ Non-Invasive Spectral Discrimination Between Bone Cell Phenotypes Used in Tissue Engineering", Journal of Cellular Biochemistry, 2004, pp. 1180-1192, vol. 92.

Pedregosa et al., "Scikit-learn: Machine Learning in Python", Journal of Machine Learning Research, 2011, pp. 2825-2830, vol. 12.

Pontiggia et al., "Optimizing in vitro culture conditions leads to a significantly shorter production time of human dermo-epidermal skin substitutes", Pediatr Surg Int, 2013, pp. 249-256, vol. 29.

Pudlas et al., "Non-invasive identification of proteoglycans and chondrocyte differentation state by Raman microspectroscopy", J. Biophotonics, 2013, pp. 205-211, vol. 6:2.

Pudlas et al., "Raman Spectroscopy: A Noninvasive Analysis Tool for the Discrimination of Human Skin Cells", Tissue Engineering: Part C, 2011, pp. 1027-1040, vol. 17:10.

Recillas-Targa, "Multiple Strategies for Gene Transfer, Expression, Knockdown and Chromatin Influence in Mammalian Cell Lines and Transgenic Animals", Molecular Biotechnology, 2006, pp. 337-354, vol. 34.

Sandbichler et al., "A Method to Evaluate the Efficiency of Transfection Reagents in an Adherent Zebrafish Cell Line", BioResearch Open Access, 2013, pp. 20-27, vol. 2:1.

Schulze et al., "A Fast, Automated, Polynomial-Based Cosmic Ray Spike-Removal Method for the High-Throughput Processing of Raman Spectra", Appl. Spectrosc., 2013, pp. 457-462, vol. 67:4.

Schevchenko et al., "A review of tissue-engineered skin bioconstructs available for skin reconstruction", J. R. Sco. Interface, 2010, pp. 229-258, vol. 7.

Tollefson et al., "Raman spectral imaging of prostate cancer: can Raman Molecular imaging be used to augment standard histopathology?", BJU International, 2010, pp. 484-488, vol. 10G.

Wikipedia, "Histology", https://en.wikipedia.org/wiki/Histology, printed from the internet Jul. 10, 2018.

\* cited by examiner

DEVICE AND METHOD FOR THE DETERMINATION OF TRANSFECTION

CROSS-REFERENCE TO RELATED APPLICATIONS

This application is the United States national phase of International Application No. PCT/EP2017/066698 filed Jul. 4, 2017, and claims priority to German Patent Application No. 10 2016 212 103.0 filed Jul. 4, 2016, the disclosures of which are hereby incorporated in their entirety by reference.

FIELD OF THE INVENTION

The present invention relates to an in vitro method for determining the transfection of a cell or group of cells, wherein said determination is performed spectroscopically. The determination comprises recording at least one Raman spectrum by means of Raman spectroscopy of the cell or group of cells. Furthermore, the present invention relates to a device for determining the transfection of a cell or group of cells, wherein the device comprises as a first unit (i) a microscope system in order to visualize the cells, as a second unit (ii) a Raman spectroscopy system in order to record a Raman spectrum of a cell or group of cells, and as a third unit (iii) an evaluation module which is coupled to the Raman spectroscopy system and which is configured to determine by means of the recorded Raman spectrum whether a cell or group of cells has been transfected.

BACKGROUND OF THE INVENTION

Transfection is a procedure that introduces foreign nucleic acids into cells to produce genetically modified cells. The introduced genetic material (typically DNA or RNA) exists in cells either stably or transiently depending on the nature of the genetic material (Recillas-Targa, 2006, Mol Biotechnol 34(3), 337-354). Several transfection methods have been developed. They can roughly be classified into biologically, chemically and physically mediated methods. The most commonly used biological method is virus-me-diated transfection (or transduction), which is highly efficient due to the viral integration into the host genome. Major drawbacks of this transfection method are immunogenicity and cytotoxicity. Chemical transfection methods are the most widely used and most popular transfection methods. Typically, these methods make use of cationic polymers, calcium phosphate, cationic lipids and cationic amino acids. The principle underlying these methods is similar: positively charged chemicals complex with negatively charged nucleic acids leading to overall positively charged chemical/nucleic acid complexes which are attracted to the negatively charged cell membrane. The introduction mechanism into the cell is believed to include endocytosis and phagocytosis. Transfection efficiency of these approaches seems to be dependent on factors such as nucleic acid/chemical ratio, solution pH and cell membrane conditions. In comparison to virus-mediated methods, there is lower efficiency, but also lower cytotoxicity and no risk of mutagenesis (Kim and Eberwine, 2010, Anal Bioanal Chem, 397, 3173-3178). Physical transfection methods use diverse physical tools to deliver the nucleic acids. These methods include, inter alia, direct micro injection, biolistic particle delivery, electroporation and laser-based transfection. Among these approaches, electroporation is the most widely used method. While the exact mechanism underlying electroporation is still unknown, it is believed that a short electrical pulse disturbs cell membranes and produces holes in the through which nucleic acids can pass (Inoue and Krumlauf, 2001, Nat Neurosci 4, 1156-1158). A relatively new addition to the group of physical transfection methods is ultrasound-mediated transfection. This method makes use of therapeutic ultra-sound (TUS), which was demonstrated to safely deliver genes into cells and nuclei. TUS appears to operate as a mechanical force delivering nucleic acids to the cell through the cytoplasmic network and into the nucleus (Haber et al., 2017, Scientific Reports, 7, 42046).

A typical transfection workflow subsequent to the transfection itself includes the plating of transfected cells, a recovery and growth period and an analysis step, which may be based on protein expression and thus include western blot analysis, report gene activity analysis or microscopic analysis, e.g. on the basis of fluorescent proteins. Alternatively, the analysis step may be based on gene expression and thus involve flow cytometry or real-time pPCR. These approaches, thus, typically involve the use of reporter or marker genes/proteins. For example, a standard fluorescence-oriented transfection efficiency determination approach is based on the calculation of percentage of transfected cells from all cells by counting transfected cells holding a Green Fluorescent Protein (GFP), as well as Hoechst-stained nuclei in recorded images of a fluorescence plate reader (Sandbichler et al., 2013, Biores Open Access, 2(1), 20-27). The method involves a 24 h regeneration period on fresh growth medium. In an alternative approach flow cytometry may be used to determine the percentage of positively transfected cells, e.g. based on GFP signals (Keith et al., 2000, BioTechniques, 28, 148-154). Also in this approach, a regeneration phase of about 1 day is required. Further approaches are based on the use of antibiotics resistance, which also require a growth period of the cells on suitable media.

All these approaches thus provide information on the efficiency of transfection only after a prolonged period of time which is mostly required for recovery of the cells and the production of markers. Moreover, the described methods make use of markers, which have to be introduced into the cells, but might not necessarily correspond to the actual gene of interest or provide an additional transgenic burden to cells, such as antibiotics resistance cassettes or fluorescent proteins.

However, there are therapeutic set-ups which require a very fast determination of the transfection efficiency. An example of such a set-up is a gene-therapy approach for the treatment of neovascular age-related macular degeneration (nvAMD). In this approach, autologous iris pigment epithelial (IPE) cells are transfected ex vivo with the PEDF gene (pigment epithelium-derived factor) and subsequently transplanted sub-retinally in the same patient within a single surgical session. Once transplanted, transfected IPE cells secrete the potent neurogenic and anti-angiogenic PEDF, regenerating a healthy retina and improving vision. Since the transfected cells have to be re-implanted into the patient within about 1 hour, the transfection efficiency has to be determined in an extremely short period of time. Moreover, the number of cells, which can be used for the determination of transfection is very limited due to the restricted number of biopsy material. Also the presence of additional marker genes such as GFP or antibiotic cassettes should be avoided for safety reasons.

There is hence a need for an improved transfection determination methodology, which allows to determine the transfection in a short period of time, on the basis of a small group of cells and without the use of an additional marker gene.

OBJECTS AND SUMMARY OF THE INVENTION

The present invention addresses this need and provides an in vitro method for determining the transfection of a cell or group of cells, wherein said determination is performed spectroscopically. The spectroscopic analysis is, in particular, based on Raman spectroscopy of cells. The inventors have surprisingly found that by using a spectroscopic analysis, in particular Raman spectroscopy (see also Hammes, 2005, Spectroscopy for the biological sciences, Hoboken, N.J., Wiley ed.), the transfection of cells can effectively be determined. This determination can be performed in a short period of time, i.e. within minutes, and with a very limited number of cells, e.g. between 60 to 500 cells. In addition, the methodology does not require the presence of any marker gene or of fluorescent proteins or the use of staining steps since it is based on a completely different principle, namely the cells' reaction on stimulation with laser radiation and the subsequent recording of Raman spectra. Thus, cells which have successfully been transfected with nucleic acids provide a Raman spectrum which differs from the Raman spectrum of cells which have not been transfected. Since the determination can be performed in a cell-by-cell manner, a very small number of cells is sufficient to provide information on the efficiency or rate of transfection. Such an approach is hence ideally suited for ex vivo transfection and re-implantation approaches, such as treatment of nvAMD. It is, furthermore, a very versatile tool, which can be used in all instances, in which transfection shall be determined, in particular in those in which fast, marker-free determination is of importance, or where only a limited number of cells is available.

In a preferred embodiment of the present invention, the determination of the transfection of a cell or group of cells comprises recording at least one Raman spectrum by means of Raman spectroscopy of said cell or group of cells.

In a further preferred embodiment, the transfection is determined within a time period of about 5 min to about 60 min.

In yet another preferred embodiment, said group of cells is a group of about 60 to about 500 cells.

In a further preferred embodiment, the group of cells to be transfected is derived from the same source and/or are is of the same type.

In specific embodiment, said cells are epithelial cells, fibroblasts, stem cells, neuronal cells, blood cells, cancer cells, skin cells or heart cells. More preferably, the cells are pigmented epithelial cells or precursors of iPS cells.

In a further embodiment of the present invention, the determination of transfection comprises recording at least one Raman spectrum by means of an integrated Raman microscope-spectroscope system of said cell or group of cells.

In a further preferred embodiment, the method as described above additionally comprises a step of morphological determination of said cell or group of cells and/or morphological comparison between the cells or within said group of cells.

In yet another preferred embodiment, said determination of transfection by recording at least one Raman spectrum is performed at a subsection of the cell. Said subsection may, preferably, be the nucleus, the cytoplasm, the cell membrane area, the mitochondria, a vacuolic structure, or the microtubule organizing center (MTC).

In a further preferred embodiment, the method as defined above additionally comprises a step of fluorescently characterizing said cell or group of cells and/or a comparison between the cells or within said group of cells.

In a further preferred embodiment, the method additionally comprises the marking of a cell of interest under microscopic view with a virtual label to allow for visual tracking.

In another preferred embodiment, the method comprises conducting a statistical evaluation of the at least one Raman spectrum.

In a particularly preferred embodiment, the method comprises a principal component analysis and/or a cluster analysis, wherein a predefined threshold value is used to differentiate between a transfected and a non-transfected cell.

In a further embodiment, the present invention relates to a method as defined herein above, wherein by means of evaluating the Raman spectrum a transfection of a cell or group of cells is identified.

In a further preferred embodiment, the evaluation of the Raman spectrum as mentioned above comprises a spectral analysis of the Raman spectrum.

In a preferred embodiment of this method, it is quantitatively determined which proportion of the cells of said group of cells is subject to a transfection. In yet another preferred embodiment, in order to quantitatively determine which proportion of the cells of said group of cells is subject to a transfection, a plurality of recorded Raman spectra are respectively subjected to a statistical analysis such as principal component analysis.

In yet another preferred embodiment, the evaluation of the Raman spectrum comprises collecting and arresting one cell in an optical trap in order to record the Raman spectrum. In a particularly preferred embodiment, said optical trap is produced by means of an excitation beam of a Raman spectroscopy system.

In a further embodiment, said cell or group of cells to be determined is located in a microfluidic system or in a microfluidic channel.

In yet another preferred embodiment, said determination of transfection is performed computer-based in order to determine transfection automatically or semi-automatically.

In a further preferred embodiment, said automatic determination comprises a scanning step, wherein Raman spectra are collected automatically in a defined area.

In yet another preferred embodiment, the method as described herein above is for determining the transfection rate of a group of cells.

In yet another preferred embodiment, said cell or group of cells is a living cell or group of living cells. Alternatively, the cell may be a fixated cell or the group of cells may be a group of fixated cells.

In another preferred embodiment, the method comprises the additional step of separating transfected and non-transfected cells. It is particularly preferred that said separated transfected cell is capable of being reintroduced or implanted into a human or animal body.

In another aspect the present invention relates to a device for determining the transfection of a cell or group of cells, wherein the device comprises as a first unit (i) a microscope system in order to visualize the cells and/or fluorescently characterize the cells, as a second unit (ii) a Raman spectroscopy system in order to record a Raman spectrum of a cell or group of cells, and as a third unit (iii) an evaluation module which is coupled to the Raman spectroscopy system and which is configured to determine by means of the recorded Raman spectrum whether a cell or group of cells has been transfected.

In a preferred embodiment of the device as described above, said device comprises as a forth unit (iv) a microfluidic component for semi-automated measurement and/or for transporting and/or separating said cells which is coupled to the Raman spectroscopy system.

In yet another preferred embodiment, said first unit and second unit is an integrated Raman microscope-spectroscope system.

In yet another preferred embodiment, said second unit is an evaluation module for performing a cluster analysis and/or a principal component analysis, which is configured to identify transfection of a cell or group of cells.

In a further preferred embodiment, the device as mentioned above is configured to perform the determination of transfection computer-based in order to determine transfection automatically or semi-automatically.

In yet another preferred embodiment, said device is configured to additionally perform the determination of cells by means of fluorescence microscopy.

In yet another preferred embodiment, the device is configured to additionally perform the determination of morphology of said cells or group of cells and/or a morphological comparison of said group of cells.

In another particularly preferred embodiment, said device is configured to determine the transfection by recording at least one Raman spectrum at a subsection of the cell. Said subsection of the cell may be the cytoplasm, the cell membrane area, the mitochondria, a vacuolic structure, or the microtubule organizing center (MTC).

It is also envisaged that the device as described above is configured to determine the transfection rate of a cell or group of cells.

In yet another preferred embodiment, the device according to the present invention is configured to perform the determination of transfection on a living cell or group of living cells, or on a fixated cell or group of fixated cells.

Finally, in particularly preferred embodiment, the present invention relates to a device which is configured to perform any of the methods as defined herein above.

DETAILED DESCRIPTION OF THE EMBODIMENTS

Figure 1:
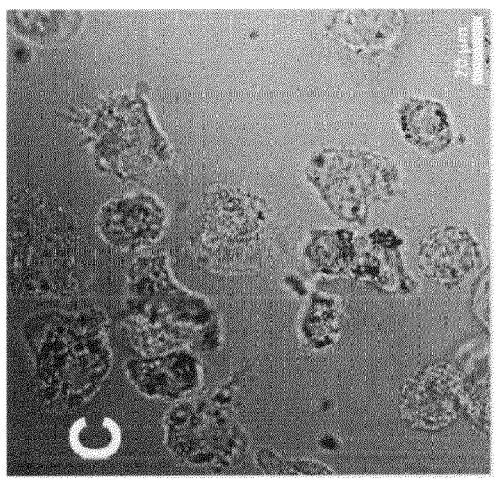
FIG. 1 shows microscopy pictures ad 60× magnification of cells from control samples (A, D), hRPE pFAR samples (B, E) and hRPE Venus samples (C, F). A-C are samples from the first batch, D-F are samples from the second batch.
Figure 1:
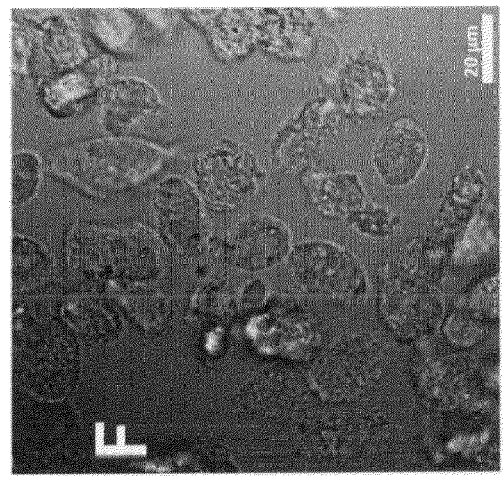
Figure 1:
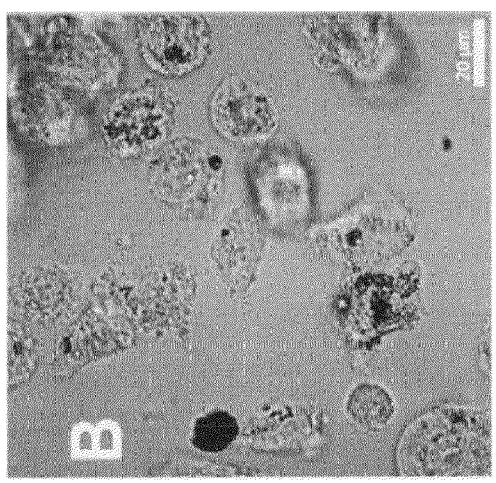
Figure 1:
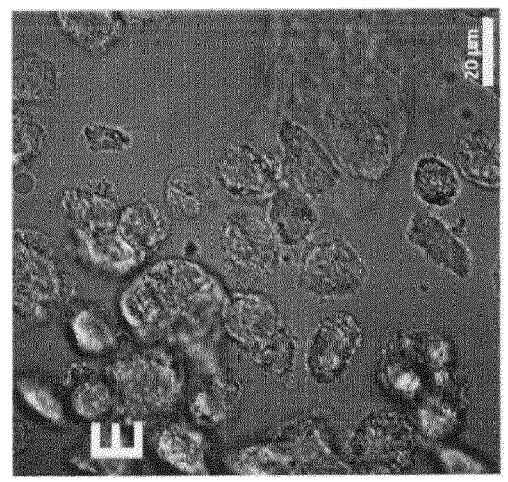
Figure 1:
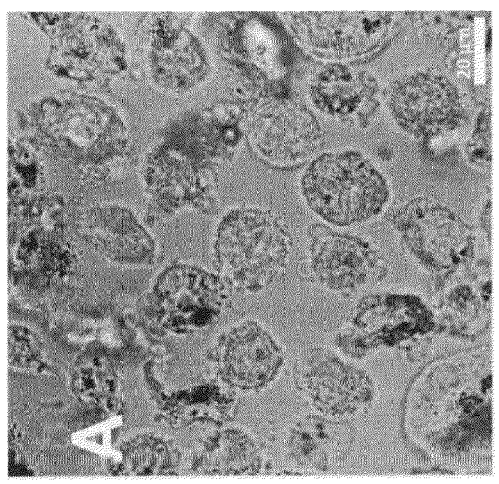
Figure 1:
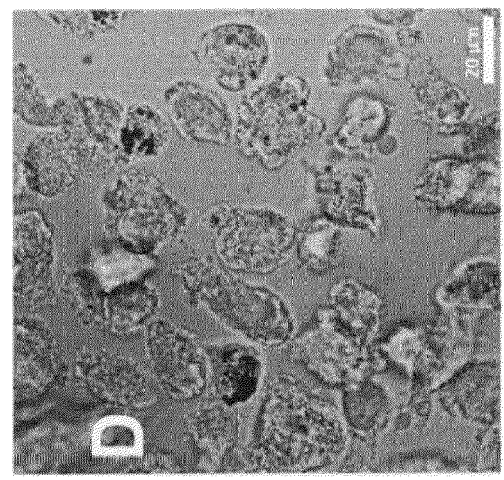

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" or "essentially consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "(i)", "(ii)", "(iii)" or "(a)", "(b)", "(c)", or "first", "second", "third" etc. and the like in the description or in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms relate to steps of a method or use there is no time or time interval coherence between the steps, i.e. the steps may be carried out simultaneously or there may be time intervals of seconds, minutes, hours, days, weeks etc. between such steps, unless otherwise indicated.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

As has been set out above, the present invention concerns in one aspect an in vitro method for determining the transfection of a cell or group of cells, wherein said determination is performed spectroscopically. The term "transfection" as used herein relates to the introduction of foreign nucleic acids into cells, preferably eukaryotic cells, to produce genetically modified cells. The nucleic acid may be any suitable nucleic acid, provided in any suitable form or format. For example, the nucleic acid may be introduced as one or more DNA or RNA molecules. Also envisaged is the introduction of DNA or RNA derivatives, e.g. chemically modified variants of DNA or RNA molecules. Moreover, the nucleic acid may be introduced as linear or circular element. In addition, the molecules may be introduced as single-stranded or double-stranded nucleic acids. For example, DNA molecules may be introduced as linear, i.e. open ended, double-stranded or single-stranded molecules. Alternatively, the DNA molecule may be introduced as circular element, preferably as circular double-stranded molecule. Typically, a circular plasmid or vector may be introduced. In case of RNA molecules, linear or circular molecules may be introduced. Typically, RNA molecules may be introduced as short double-stranded linear elements. Also envisaged is the employment of mixtures or hybrids of DNA and RNA molecules. The nucleic acids may, in certain embodiments, be complexed with, or co-introduced with, additional factors, e.g. proteins, small molecules, polymers etc. The transfected molecules may subsequently be integrated in the genome of a cell, e.g. be integrated in a single copy or in multiple copies. In case of integration into the genome, the transfection is called stable, providing stable transfectants. Alternatively, the transfected molecules may be present outside of the genome of a cell, i.e. they do not integrate into the genome. This transfection type is referenced as transient transfection, providing transient transfectants. Typically, the transient transfection allows for expression of genes for a limited period of time, e.g. for about 5 min to 96 hours.

According to the present invention different transfection approaches are envisaged. Thus, any suitable biological, chemical or physical transfection method known to the skilled person may be used for a transfection.

Examples of suitable transfection methods include biological methods such as virus-mediated transfection, wherein a modified virus is contacted with a cell and subsequently integrates DNA into the genome of the cell. Examples of suitable viruses include Herpes simplex virus, Retroviruses, Lentivirus, Adenovirus, Ando-associated virus, Vaccinia virus and Sindbis virus.

Suitable chemical transfection methods include cationic lipid based transfection, calcium phosphate based transfection, or cationic polymer based transfection. Cationic lipids are amphiphilic molecules that have a positively charged polar head group linked, via an anchor, to a non-polar hydrophobic domain typically comprising two alkyl chains. Electrostatic interaction between the positive charges of the cationic lipid head groups and the negatively charged phosphates of the DNA backbone allow nucleic acids to spontaneous associate with cationic lipids. Resulting liposomes may then be introduced into cells via endocytosis or merging with membranes, which also comprise a phospholipid bilayer. Calcium phosphate based transfection typically involves the mixing of DNA with calcium chloride, the subsequent addition of this mixture to a buffered saline/phosphate solution and the incubation of the mixture at room temperature. Thereby a precipitate is generated which is dispersed onto the cells and is take up by the cells via endocytosis or phagocytosis. Cationic polymer based transfection is based on the use of cationic molecules which do not contain a hydrophobic moiety and are soluble in water. These polymers are provided in different lengths and geometries, e.g. as linear such as spermine or polylysine, branched or spherical molecules. They may further include polyethyleneimine (PEI) or dendrimers. These polymers are assumed to effectively condense nucleic acids. A further example of a suitable cationic polymer is DEAE-dextran, i.e. a molecule which tightly associates with negatively charged nucleic acids. The correspondingly positively charged DNA-polymer complex may come into close proximity of the negatively charged cell membrane. Subsequently, the complex is typically taken up by the cell via endocytosis or macropinocytosis.

Suitable physical transfection methods include magnet-mediated transfection, electroporation, biolistic particle delivery, direct micro injection, and laser-based transfection. In magnet-mediated transfection magnetic forces are sued to deliver the nucleic acid into the cells. Firstly, nucleic acids are associated with magnetic nanoparticles. Upon the application of magnetic forces the nucleic acid-particle complex is driven towards and into the cell, where the cargo is released. Electroporation, one of the most popular transfection methods, which is also preferred in the present invention, is based on the exposure of cells with a high-intensity electrical field which temporarily destabilizes the membrane. During this time the membrane is highly permeable to exogenous material in the surrounding media. Nucleic acids can subsequently enter the cell through the occurring holes in the membrane. Upon tuning off the electrical field, the pores in the membrane are believed to reseal, thereby enclosing the DNA. A biolistic transformation is based on the delivery of nucleic acids into cells via high velocity nucleic acid-coated microparticles, e.g. gold particles. The system typically uses high-pressure helium, released by rupture disk, and partial vacuum to propel the carrier towards the target cell. DNA coated particles then penetrate the cell. A further option is direct micro injection of nucleic acids. In this approach an injecting pipet is used to directly introduce naked DNA into a cell. Laser-based transfection or laserfection typically uses laser light to transiently permeabilize a large number of cells in a very short time. Substances including nucleic acids, but also ions, small molecules, dextrans etc. can be optoinjected into a cell.

The term "spectroscopic determination" as used herein relates to the determination of transfection of a cell or group of cells by spectroscopic means, i.e. by studying the interaction of one or more transfected cells and electromagnetic radiation. The determination typically includes interaction with radiative energy as a function of its wave-length or frequency. By stimulating cells, i.e. transfected cells, an emission or response of the cells is generated which can subsequently be recorded and analysed. The method, in principle, is based on the simultaneous performance of one or more control experiments or the use of control situations, e.g. with cells that have not been transfected to allow for a comparison of the spectral analysis of transfected and non-transfected cells. As has been described herein below, a variant of the method without concomitant controls is also possible and envisaged herein. Differences in emission spectra may, for example, be based in differences or changes in the metabolome of a cell. Without wishing to be bound by theory, it is assumed that the transfection of a cell will lead, within a short period of time, to changes in the presence and/or amount of metabolic entities in a cell, e.g. proteins, DNA, organic molecules etc. Such changes can advantageously be detected and registered spectroscopically in a non-invasive and fast manner.

The term "determining the transfection of a cell" relates to the analysis of a cell with respect to its transfection status. The determination can be performed with single cells by spectroscopic means as mentioned above, or below. The determination is typically based on comparison operations with suitable control cells or control situations, or with suitable comparison patterns. A typical control would be the analysis of a cell or more than one cell, which has not been transfected. Further controls may include the analysis of different cell types, cells from different patients or derived from different sources etc. Upon analysis of a group of cells, preferably of a group of cells of the same cell type, or derived from the same source or the same patient, it is further possible to obtain a value for the percentage or ratio of transfected cells vs. non-transfected cells, i.e. a transfection rate.

In preferred embodiments, the spectroscopic determination is based on the recording of a Raman spectrum by means of Raman spectroscopy. The term "Raman spectroscopy" as used herein relates to a spectroscopic analysis which essentially relies on the observation of vibrational, rotational, and other low-frequency modes in a system. The technique is typically used to provide a structural fingerprint of molecules. It relies, in principle, on Raman scattering, i.e. inelastic scattering, of monochromatic light, from a laser in the visible, near infrared, or near ultraviolet range. The laser light typically interacts with molecular vibrations, phonons or other excitations in a system, e.g. a cell, resulting in the energy of the laser photons being shifted up or down. The shift in energy gives information about the vibrational modes in the system. Typically, a sample, i.e. a cell, is illuminated with a laser beam. Electromagnetic radiation from the illuminated entity is collected with a lens and sent through a monochromator. Elastic scattered radiation at the wavelength corresponding to the laser line (i.e. Rayleigh scattering) may be filtered out, e.g. by a notch filter, an edge pass filter, or a band pass filter, while the rest of the collected light is dispersed onto a detector. In a typical embodiment a Raman spectroscopy system may be used which comprises a light source which can in particular be a laser. The light source is typically configured to output an excitation beam. The excitation beam can for example have a wavelength in the range between 700 nm and 1064 nm, e.g. approximately 785 nm. Subsequently, a Raman spectrometer receives light scattered on the sample, e.g. a cell, by Stokes processes and/or Anti-Stokes processes. Furthermore, the approach may comprise the use of a Raman spectrometer comprising a diffractive element and an image sensor in order to record the Raman spectrum of the sample, e.g. cell. Furthermore, additional elements may be employed to perform the analysis, e.g. focusing optical elements, which can be designed as lenses, and/or diaphragms. In order to identify transfection In a specific embodiment, the determination method according to the present invention comprises conducting a statistical evaluation of the at least one Raman spectrum, preferably of a plurality of Raman spectra, e.g. between 10 to 1000 spectra. The plurality of spectra may either be obtained for a single cell, or for a group of cells, e.g. one spectrum may be obtained for one cell. The statistical evaluation is preferably a quantitative determination which proportion of the cells or a group of cells as mentioned herein is subject to a transfection.

The Raman spectrum can, in a specific embodiment, be evaluated by a spectral analysis. For example, an analysis of mean value spectra, a principal component analysis and/or a support vector machine (SVM) can be used in order to determine whether a transfection has occurred in a cell or group of cells.

The statistical evaluation may, for example, be a principal component analysis (PCA) or a hierarchical or non-hierarchical cluster analysis for each of the Raman spectra detected. Typically, in the "principal component analysis (PCA)", a coordinate transformation in the N-dimensional data space is determined in such a way that the analysed entity of data points is spread along its most statistically relevant (e.g. variance-containing) coordinate axes in the transformed coordinate space. These coordinate axes define the principal components. The first principal component PC-1 typically defines the axis with the sharpest differences between the different groups of Raman spectra. Alternatively or additionally, it can be determined whether a transfected or non-transfected cell is present based on the second principal component PC-2 or another low principal component.

Accordingly, by means of a statistical analysis such as the principal component analysis or a cluster analysis, as mentioned herein, it can be determined whether the pattern of Raman peaks contained in the Raman spectrum is characteristic of a transfected cell or a non-transfected cell. Alternatively or additionally, it can be determined whether the pattern of Raman peaks contained in the Raman spectrum is characteristic of the presence of transfection as a "photonic fingerprint."

A principal component analysis may hence be performed for a Raman spectrum or a plurality of Raman spectra which have been recorded from the sample, e.g. a cell or group of cells.

The determination of whether the Raman spectrum is characteristic of a transfected or non-transfected cell may hence not be based on individual Raman peaks, but rather on a plurality of Raman intensities distributed evenly or unevenly over the Raman spectra at a plurality of Raman wavenumbers, yielding a characteristic spectral pattern. Thus, by means of a statistical method such as the principal component analysis, as mentioned above, or other statistical methods such as hierarchical or non-hierarchical cluster analyses, one can take advantage of the fact that the Raman spectrum as a whole shows characteristics that are indicative of a transfected or non-transfected cell and can thus serve as a measure of successful transfection.

In addition, the spectral patterns may also indicate the vitality and/or functionality of a cell. For example, when cells start to decay or change their functionality the composition of biomolecules within the cell changes which also is expressed in a change of the spectral pattern. Accordingly, valuable information about the vitality of the cells can be measured and provided by using Raman spectroscopy. For example, the spectral pattern may allow to identify vital cells versus dead cells or cells that start to decay or become apoptotic or necrotic, and which cannot be considered to be successfully transfected.

The patterns in a Raman spectrum can be defined by one or a plurality of parameters selected from the group composed of the wavenumbers at which the Raman peaks are located, the peak heights, the flank steepness of the peaks, the distances between the peaks, and/or combinations of peaks in one or a plurality of Raman spectra. For evaluation of one or a plurality of Raman spectra detected in a sample, e.g. one cell, one can determine whether these peak(s) are situated in a space, according to a principal component analysis, in an area assigned to transfected cells or in another area assigned to non-transfected cells.

For example, by means of a statistical evaluation, each Raman spectrum can be assigned to a point in an N-dimensional data space, wherein $N\gg1$, e.g. $N>100$. The N-dimensional data space can be the data space spanned in a principal component analysis by the various principal components. Furthermore, one can determine from reference spectra, e.g. control experiments or previously recorded spectra, in which areas of the N-dimensional data space Raman spectra are arranged in clusters for transfected cells and in which other areas of the N-dimensional data space Raman spectra are arranged in clusters for non-transfected cells.

In addition, or alternatively, Raman spectra in at least individual Raman peaks can be compared with reference data in order to determine whether a transfected cell is present. Determination of the peaks is not limited to the intensity of individual Raman peaks, but can also be carried out for example for the distance of a data point in an N-dimensional data space of a principal component analysis from the area in the N-dimensional data space.

An assignment to different types of transfection (i.e. transfection group vs. non-transfection group) can further take place for a cluster analysis or for a different analysis of the recorded Raman spectra for example by means of different wavenumber ranges. In order to identify transfected cells, at least one wavenumber in the wavenumber range of 1250-1450 $cm^{-1}$ and 1620-1700 $cm^{-1}$ can for example be evaluated in order to determine whether a transfection has occurred or not. In addition at least one wavenumber from one or a plurality of wavenumber ranges of 1650 to 1600 $cm^{-1}$, from 1350 to 1250 $cm^{-1}$, from 1180 $cm^{-1}$ to 1120 $cm^{-1}$, from 1100 $cm^{-1}$ to 1050 $cm^{-1}$, from 930 $cm^{-1}$ to 890 $cm^{-1}$ or from 700 $cm^{-1}$ to 650 $cm^{-1}$ may be evaluated. In order to perform the cluster analysis, the mentioned wavenumber ranges do not necessarily have to be evaluated, but rather other principal components can also be evaluated.

In a further preferred embodiment, the method of the present invention includes a statistical method such as a principal component analysis and/or a cluster analysis, wherein a predefined threshold value is used to differentiate between a transfected and a non-transfected cell. The term "threshold value" as used herein relates to a cut-off value which can be been introduced into the statistical evaluation. The threshold value can, for example, be defined using a confidence interval and/or other statistical or empirical means around a reference cell or group of cells. Typically, the cut-off is defined as the 95% confidence interval around the center of control samples, e.g. non-transfected cells. Accordingly, cells that show a principal component score that is outside of these limits may be assumed to be differentiated or distinguishable from the control group. The nature and number of control cells may be varied in compliance with the transfection protocol, nature of host cells and further suitable parameters. In further embodiments, corresponding values may be used as reference values (without the necessity of performing controls) if previously obtained values indicate that there is no difference between control groups to be expected, or if similar control groups have been measured before.

It is one of the advantageous features of the present invention that the determination of the transfection is performed in a short period of time after the transfection has taken place. Typically, the determination may be performed in a period of about 1 min to about 60 min, e.g. in a period of time of about 1 min, 2 min, 3 min, 4 min, 5 min, 6 min, 7 min, 8 min, 9 min, 10 min, 15 min, 20 min, 25 min, 30 min, 40 min, 50 min, 60 min or more. The term "period of time" as used herein refers to the time which has passed after the transfection procedure has been finished. In particular, the method does not require a recovery or material production step, as in transfection determination methods of the prior art.

According to another advantageous feature of the present invention, the determination of transfection, in particular the determination of transfection rates or transfection efficacy, is performed with a small group of cells. For example, a group of 15 to 20 cells may be used for the determination approach. It is preferred that the group of cells is a group of about 60 cells or more. Since every cell is analysed individually, the number of cells to be analysed in order to be capable of calculating a transfection rate, is mainly dependent on the implementation of the transfection, i.e. the quality of the transfection process. Thus, should the transfection process only allow for one transfected cell in 20 cells treated, at least 20 cells, preferably at least 30 or 40 cells, should be analysed. Likewise, if the transfection process only allows for one transfected cell in 100 cells treated, at least 100 cells, preferably at least 150 or 200 cells, should be analysed etc. The number of cells to be analysed, may either be predetermined, e.g. on the basis of previous results, or be determined in accordance with the results obtained from the ongoing measurement. In further embodiments, the number of cells to be analysed may be in the range of 15 to 500 cells, or 60 to 500 cells, e.g. 20, 30, 40, 50, 60, 70, 80, 90, 100, 200, 300, 400, 500 or more cells. The present invention also envisages the use of a number of cells in between the mentioned values.

The cells to be analysed may be derived from the same source, e.g. the same patient, the same group of patients, the same hospital, the same surgeon, the same region etc. Alternatively or additionally, the cells may be of the same type. The term "type" as used herein relates to phenotype or histological/morphological aspect of a cell. The cells may, for example, be stem cells, induced stem cells, fibroblasts, epithelia cells, tumor cells, blood cells, skin cells, heart cells etc. with specific functions. In particularly preferred embodiments, the cells may be pigmented epithelial cells. Also preferred is the use of precursors of induced pluripotent cells (iPS cells), e.g. fibroblastic cells, keratinocytes or peripheral blood cells, or renal epithelial cells etc. which can be reprogrammed by introducing a specific set of pluripotency-associated genes, or "reprogramming factors".

The cells may generally be living cells. The term "living cell" as used herein relates to any form of cell which is metabolically active. This also includes apoptotic, necrotic or decaying cells, as well as vital cells, unless these cells have ceased to be metabolically active. In further embodiments, also dead cells, i.e. metabolically inactive cells, may be analysed. However, such cells cannot be or have not been successfully transfected and may thus be counted as non-transfected cells, e.g. if in a group of cells a certain proportion of cells is identified as dead, e.g. in accordance with the above outlined visual and spectral analysis approach. In further embodiments, the cells may have been fixated. The fixation may have taken place immediately after transfection, or at any point in time after transfection. Any suitable fixation protocol known to the skilled person may be used in order to obtain fixated cells in accordance with the present invention. It is preferred that the fixation protocol preserves the metabolome as good as possible. One example would be the fixation with paraformaldehyde, which is preferred. Further alternatives thereto, also future developments of specific metabolome preserving fixation protocols are envisaged herein.

In another embodiment transfected cells as identified by the present method may be separated and isolated to be subsequently re-introduced or re-implanted in the subject or patient they are originally derived from, e.g. in the human or animal body. In the alternative, these cells may also be introduced in a different patient or subject, or stored for any suitable time until implantation in a suitable location. These cells are accordingly sterile, i.e. they are not affected by the presence of germs or pathogens of any type. Furthermore, the cells are provided in a non-toxic environment, which can advantageously be implemented with the present methodology, since no invasive or chemical interaction step is necessary to determine their transfection state. By performing the method in a sterile manner, e.g. in sterile compartments, and by avoiding exposure to toxic substances, a re-implantation of transfected cells, i.e. of cells which have been identified positively according to the present invention, becomes possible.

In a further preferred embodiment the determination comprises recording at least one Raman spectrum by means of an integrated Raman microscope-spectroscope system of a cell or group of cells as defined herein above. An "integrated Raman microscope-spectroscope system" according to the present invention refers to a microscope which comprises in the optical path optical elements for laser stimulation and for the recording of one or more Raman spectra, e.g. as defined herein above. The integrated system thus allows for a determination of features of a cell at visible wavelengths, i.e. to visualize the cells. Accordingly, morphological features of a cell may be determined via the microscopic module of the integrated system, while one or more Raman spectra of the same cell may at the same time be determined with the help of the optical elements as mentioned above.

In a specific embodiment of the present invention, the determination comprises a step of morphological determination of said cell or group of cells. The determination is based on the use an integrated Raman microscope-spectroscope system as described above, or a device according to the present invention as described in detail below, which allows for a morphological determination of said cell or group of cells. For example, by determining, inter alia, one or more of form, size, diameter, optical density, presence of subcellular elements such as vacuoles, nuclei, membrane area, mitochondria, cytoplasm etc. and optionally by comparing measured values with reference values, e.g. derived from a morphological database or from previous measurements, a histologic or phenotypic classification of a cell may be achieved. In an additional step, two or more cells to be determined may be compared morphologically. For example, if a cell has morphologically been classified, it may be determined if a second or further cell falls within the same classification or belongs to a different group, i.e. may be classified differently, thus representing a different cell type and/or different cell state or activity etc. In addition, or alternatively, the morphological determination may be used to confirm or verify information about the vitality of the cells, as measured and provided by using Raman spectroscopy. For example, if spectral patterns have been obtained which indicate that a cell is dead cells or that cells start to decay or become apoptotic or necrotic, such information may be compared and thereby be confirmed or corrected by said morphological determination. This approach additionally allows for a quality control step within a transfection workflow, thus alerting the operator to stop subsequent steps, e.g. if a specific threshold of either non-transfected and/or dead, decaying, apoptotic or necrotic cells has been reached within the analysed group of cells. The threshold may be at about 30 to 60% of the cells, preferably at about 30, 35, 40, 45, 50, 55, or 60% of cells within a group of cells analysed.

In further specific embodiments, a cell which has been visualized and/or morphologically been determined may be marked under the microscopic view as cell of interest. Such a marking may be a virtual marking or be based on the use of a virtual label. Typically, such a marking may be implemented by a computer-based or software solution, which records a picture of cells and highlights a cell of interest. Such a cell may subsequently be tracked, e.g. if the cell is moving or floating in a group of cells.

In further particularly preferred embodiments, the method according to the present invention additionally comprises a step of fluorescently characterizing said cell or group of cells and/or a comparison between the cells or said group of cells. The fluorescent characterization may be performed with a fluorescent microscope, preferably with a device as defined herein below. The "fluorescent characterization" as mentioned comprises a stimulation of a cell with a suitable excitation wavelength and the receiving of fluorescent signals from the cell. This step may, in particular, be used in case of transfected nucleic acids which allow for the expression of a fluorescent marker, e.g. GFP, YFP, Venus etc. Any suitable fluorescent marker known to the skilled person may be used in this context. The same cell which has been fluorescently characterized may further be subjected to a spectroscopic analysis as defined herein, in particular a Raman analysis. Since the positive identification of a fluorescent cell means that such a cell has been transfected successfully, a corresponding Raman spectrum of said cell may be used as positive definition of a Raman spectrum which indicates successful transfection. In such cases the employment of empty controls, e.g. of cells which have not been transfected, can be circumvented or skipped. In a specific embodiment, a group of cells may first be transfected with a construct allowing for the expression of a fluorescent protein marker, e.g. GFP. The transfection rate in this group is determined by fluorescently characterizing these cells. All fluorescent cells are assumed to have been transfected. Subsequently, a Raman spectrum is obtained from these fluorescent cells. This spectrum is subsequently used, e.g. for a second transfection approach with a non-fluorescent gene of interest, as positive example of successful transfection. Raman spectra obtained with cells transfected in said second approach with a non-fluorescent gene of interest may accordingly be identified as being transfected, if the same or a very similar Raman spectrum as in case of the previously analyzed fluorescent cells is detected.

In specific embodiments, additional controls with non-transfected cells may be performed.

In further embodiments said method of determination of transfection by recording at least one Raman spectrum is performed at a subsection of the cell. The subsection of the cell may be determined morphologically, e.g. with the help of the integrated Raman microscope-spectroscope system as described above, or a device according to the present invention as described in detail below. The term "subsection" as used herein relates to a subcellular compartment of a cell, such as the nucleus, a vacuole or vacuolic structure, a mitochondrion or several mitochondria, the cytoplasm or a part of it or the microtubule organizing centre (MTC). Also encompassed are cellular parts such as the cell's membrane area, i.e. part of the cell which is located at the cell's rim. The diameter or thickness of said rim region of a cell is assumed to be typically in the range of about 1 to 3 µm. By determining subsections of a cell as described above, Raman spectra of components enriched in said sections may preferentially be obtained. For example, if the determination is performed at the nucleus, mainly Raman spectra of nucleic acids may be obtained. If, in a different example, the determination is performed in a membrane area of a cell as defined above, mainly Raman spectra of lipids may be obtained.

The method according to the present invention also envisages determination of transfection at more than one subsection of a cell, e.g. at the nucleus and at a membrane area of a cell. In such an approach, obtained spectroscopic results may be combined. Alternatively, such spectra may be compared separately with corresponding spectra of a second or further cell, or with one or more controls.

In a further embodiment a method for determination of transfection according to the present invention includes the evaluation of the Raman spectrum by collecting and arresting at least one cell in an optical trap in order to record its Raman spectrum. The term "optical trap" as used herein relates to a single-beam gradient force trap or optical tweezer, which uses a highly focused laser beam to provide an attractive or repulsive force. The optical trap may be produced by the excitation beam of the Raman spectroscopy system or a beam of electromagnetic radiation different therefrom. For example, a focal point of a beam may produce an optical trap potential, in which a cell is collected for the Raman spectroscopy. The focal point can be produced by the excitation beam, which is output by a light source. In such an embodiment, the excitation beam can thus be used both as excitation for the Raman scattering and for producing the optical trap. Alternatively, the optical trap can also be produced by a separate beam. The optical trap may either collect and arrest one cell or a group of cells. The optical trap may further be used to move cells. It may hence be employed to separate cells which have been identified as transfected cells from those which have been identified as non-transfected cells. The term "arrest" as used herein relates to a brief holding of a cell at a specific position to allow for the performance of Raman spectroscopy.

In a further embodiment, the cells or group of cells may be provided in a micro-fluidic system or microfluidic channel. The term "microfluidic system" as used herein relates to a system in which a precise control and manipulation of fluids is possible. Typically, the systems are based on capillary forces. Alternatively, active elements such as micropumps or microvalves may be used. The microfluidic systems are provided in a sub-millimeter scale. A microfluidic system as envisaged by the present invention may comprise several modules which may be connected by channels. For example, the system may comprise a module where transfection of cells takes place. It may further comprise a reservoir for cells and a reservoir for fluids or buffers etc. It may, in addition, comprise zones or modules where nucleic acids can be isolated and analysed, a microarray module, a cell staining module, a module which is configured to allow antibody binding, a microtiter plate allowing for contacting of cells with a substance, or which allows for cultivation of cells or any other suitable module or element. For the performance of the determination of a transfection, the microfluidic system may comprise a channel or sector, which is connected to a microscope according to the present invention and/or a Raman spectroscopy system, or an integrated Raman microscope-spectroscope system. Preferably, said channel or zone allows for slowing down of liquid movements to allow for optical/spectral analysis of the cells. Furthermore, the channel or zone is configured to allow the application of an optical trap as defined herein above. In specific embodiments, the channel or zone may be connected to one or more reservoirs which may receive cells which have been separated, e.g. by use of the optical trap, according to the transfection state, or any other parameter, e.g. vitality, cell type etc.

In a further particularly preferred embodiment, the determination of transfection is performed in an automated or semi-automated manner. To be capable to determine transfection automatically or semi-automatically, method steps as mentioned herein above may be performed in a computer-based manner. For instance, once cells enter a detection, e.g. of a microfluidic system as described above, images may be acquired. By using suitable image analysis software and/or cell tracking software, specific cells may be recognized, highlighted and/or be virtually labelled. The corresponding activities may be performed automatically, or, in certain embodiments semi-automatically, e.g. by requiring a human interaction or by asking for confirmation by the operator. Upon completion of these steps, additional analysis steps may automatically be started such as performance of stimulation of the cells, spectral, e.g. Raman analyses, recording of spectra, e.g. Raman spectra, recording of fluorescence of cells, classification of cells, e.g. according to transfection state as transfected or non-transfected cells, quality control checks, comparison steps with visual images etc. Correspondingly obtained information may further be accumulated, stored in suitable databases or on suitable servers, transferred to remote systems or entities etc. It is preferred that all images taken are saved on a local hard disk and/or on a cloud server, at least until a sample or group of cells has entirely been analysed, preferably until the entire procedure connected with the transfection step has been finished. The saving time may further be extended for documentation purposes.

In further embodiments, the automatic determination may comprise a scanning activity, wherein Raman spectra are collected automatically in a defined area. The defined area may, for example, but a sub-portion of the zone where the cells are located. By scanning the cells in a defined area, it is possible to determine how many cells within the area are transfected. The scanning approach may be connected with the addition of a virtual label to each cell, i.e. a tracking activity. The scanning may include the performance of spectral analyses as defined herein, e.g. Raman spectroscopy as mentioned above.

In further embodiments, the method includes an automated or semi-automated separation step for the analysed cells. For example, by making use of an optical trap or by making use of microfluidic movements, cells which have been identified as transfected cells may be separated from those cells, which have been identified as non-transfected cells. The separation step may be performed such that a visually tracked cell is automatically labelled as being transfected and subsequently moved to a specific zone of the microfluidic system, e.g. a reservoir for similar cells.

In a further aspect the present invention relates to a device for determining the transfection of a cell or group of cells, wherein the device comprises as a first unit (i) a microscope system in order to visualize and/or fluorescently characterize the cells; as a second unit (ii) a Raman spectroscopy system in order to record a Raman spectrum of a cell or group of cells; and as a third unit (iii) an evaluation module which is coupled to the Raman spectroscopy system and which is configured to determine by means of the recorded Raman spectrum whether a cell or group of cells has been transfected.

The microscope system in order to visualize and/or fluorescently characterize the cells may comprise a light source, which can either be a laser or a light source for visual detection. The laser may, in particular, be a laser which allows to stimulate fluorescent markers such as fluorescent proteins or fluorescent stains or fluorescent small molecules. The microscope system may thus be a system capable of fluorescence microscopy. The microscope system may receive from the sample, e.g. a cell to be analysed, a form of visual reflection and/or a fluorescent reaction to the stimulation. The microscope may further comprise elements known to the skilled person such as, for example, focusing optical elements which can be designed as lenses, and/or diaphragms. The microscope system may further be connected to an evaluation module as defined herein below.

The Raman spectroscopy system may comprise a light source which can in particular be a laser. The light source is configured to output an excitation beam. The excitation beam can for example have a wavelength in the range between 700 nm and 1064 nm, e.g. approximately 785 nm. A Raman spectrometer receives light scattered on the sample, e.g. a cell as defined above, by Stokes processes and/or Anti-Stokes processes. The Raman spectrometer can comprise a diffractive element and an image sensor in order to record the Raman spectrum of the sample. The Raman spectroscopy system can comprise further elements in a manner known per se, for example focussing optical elements which can be designed as lenses, and/or diaphragms.

The evaluation module can be a computer or can comprise a computer. The evaluation module may be coupled to the Raman spectroscopy system and/or the microscope system as defined herein above. The evaluation module can control the recording of the Raman spectrum by the Raman spectroscopy system, as well as the visual or fluorescent recording of the cells. In addition, the evaluation module comprises an interface in order to receive data from an image sensor of the Raman spectroscopy system or the microscope system. The evaluation module, in further embodiments, may comprise an integrated semi-conductor circuit which can comprise a processor or controller and which is configured to evaluate the recorded images or Raman spectra in order to determine the transfection of a cell or group of cells, or the morphology of the cells. In further embodiments, it may be capable of determining the subsection of cell, where the Raman analysis takes place. The integrated semi-conductor circuit is configured to determine by means of the Raman spectrum, optionally in combination with interpretation of visual images, whether a transfection of a cell has taken place. The integrated semi-conductor circuit can be configured in particular in order to determine by means of evaluating the Raman spectrum whether a transfection has taken place, and/or whether the cell is vital or shows signs of apoptosis, necrosis or decay. The integrated semi-conductor circuit can further be configured to determine by means of evaluating the Raman spectrum whether a cell death of the transfected cells has occurred.

In further embodiments, the integrated semi-conductor circuit as mentioned above can be configured to identify the presence or absence of determined Raman peaks or to determine the spectral weight of Raman peaks which relate to the transfection of cells. For example, the integrated semi-conductor circuit can identify and/or further evaluate Raman peaks, which are assigned to the transfection state, or which are assigned to a cell death. The integrated semi-conductor circuit can be configured to evaluate for example the Raman spectrum in at least one predefined wavenumber range, e.g. the Raman spectrum in the wavenumber range between 1250-1450 $cm^{-1}$ and 1620-1700 $cm^{-1}$ in order to determine whether a transfection has taken place.

In specific embodiments, the integrated semi-conductor circuit further can be configured to automatically determine the fluorescence of a cell by analysing the fluorescent reaction of a cell upon stimulation with a suitable excitation beam.

In specific embodiments, the evaluation module can be configured to perform a cluster analysis or a principal component analysis. It is preferred that the evaluation module is configured to identify transfection of a cell or group of cells by performing such cluster analysis or principle component analysis.

The evaluation module can further comprise a memory in which comparative data is stored which the integrated semi-conductor circuit can use when evaluating the Raman spectrum. Information regarding the position and/or the spectral weight of different Raman peaks for analysed cells can be stored in a non-volatile manner in the memory of the module. Alternatively or additionally, the information regarding the position and/or the spectral weight of different Raman peaks for the analysed cells can be determined by the module by means of methods of supervised learning or other machine learning techniques.

The evaluation module can comprise an optical and/or acoustic output unit, via which the information dependent on the analysis of the Raman spectrum is output, which shows whether or not a transfection has occurred in a cell or with which rate a transfection has occurred in a group of cells. The output unit can also be structurally integrated into a housing of the evaluation module or of the Raman spectroscopy system.

In further embodiments, a threshold value for a transfection state can be stored in a non-volatile manner in the evaluation module. If the proportion of non-transfected cells after the result of the principal component analysis or a different cluster analysis, exceeds the threshold value, the evaluation module automatically identifies that the group of transfected cells is not suitable for re-implantation into a subject or patient.

In specific embodiments the device according to the present invention, in particular the evaluation module is configured to determine the transfection rate. The transfection rate may be determined on the basis of a calculation algorithm based on analysis results for positive transfection and negative transfection identification in the measured cells, in particular the group of measured cells, e.g. in a specific area.

In specific embodiments, the device according to the present invention, in particular the evaluation module is configured to determine the transfection by recording at least one Raman spectrum at a subsection of the cell. The evaluation module is, in specific embodiments, configured to determine at least one Raman spectrum in the cytoplasm, the cell membrane area, the mitochondria, a vacuolic structure, and/or the microtubule organizing center (MTC).

In a further embodiment, the device according to the present invention additionally comprises a microfluidic component. The microfluidic component may, for example, be configured to allow semi-automated or automated measurement of cells. It may in addition or alternatively be configured to transport cells. It may, in addition or alternatively, be configured to separate cells. This component is, in specific embodiments, coupled to the Raman spectroscopy system as mentioned herein above. It may alternatively or further be coupled to the microscope system as mentioned herein above. It may further or alternatively be coupled to the evaluation module as defined herein above. The microfluidic component may, in preferred embodiments, correspond to a microfluidic system as defined herein above. Briefly, it may allow for a precise control and manipulation of fluids. It may further comprise active elements such as micropumps or microvalves. In further embodiments, it may comprise several modules which may be connected by channels. For example, it may comprise a module where transfection of cells takes place. It may further comprise a reservoir for cells and a reservoir for fluids or buffers etc. It may, in addition, comprise zones or modules where nucleic acids can be isolated and analysed, a microarray module, a cell staining module, a module which is configured to allow antibody binding, a microtiter plate allowing for contacting of cells with a substance, or which allows for cultivation of cells or any other suitable module or element. For the performance of the determination of a transfection, it may comprise a channel or sector, which is connected to a microscope according to the present invention and/or a Raman spectroscopy system. Preferably, said channel or zone is configured to slow down liquid movements to allow for optical/spectral analysis of the cells.

In a preferred embodiment one or more of the above mentioned units of the device are integrated. For example, the device may be an integrated Raman microscope-spectroscope system. There may further be an integration with the evaluation module. There may also be an integration with the microfluidic component as defined above. The elements may, in specific embodiments, also be used separately, or be combinable as removable but connectable units.

In a further preferred embodiment, the device according to the present invention may be configured to provide an optical trap. The optical trap can be produced by the excitation beam of the Raman spectroscopy system or a beam of electromagnetic radiation different therefrom. The excitation beam can thus be used both as excitation for the Raman scattering and for producing the optical trap. Alternatively, the optical trap can also be produced by a separate beam. The Raman spectroscopy system can also comprise a light conductor, for example an optical fibre, by means of which the excitation beam and/or the Raman scattered light is guided. The light conductor can be positioned such that the excitation beam leaving said light conductor produces the optical trap with a focal point.

In yet another preferred embodiment, the device according to the present invention is configured to perform the determination of transfection on a living cell or group of living cells, or on a fixated cell or group of fixated cells. For example, the device may be configured to perform the analysis of living cells by providing within the microfluidic component a zone which slows down the movement of cells. Further-more, it may comprise a reservoir for living cells which can be re-implanted to a patient. In case of fixated cells, the microfluidic component may comprise a module which allows to fixate cells, e.g. automatically or semi-automatically, preferably according to the procedure mentioned above.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1

AMD Detection with Raman Spectroscopy

Introduction

Disease Pathology

Age-Related Macula Degeneration (AMD) is a major cause of blindness in elderly people in industrialised countries. The exudative ("wet") form of AMD is characterised by the presence of choroidal neovascularisation (CNV). This CNV is triggered by an imbalance of angiogenic and anti-angiogenic factors in favour of angiogenesis. Most prominent molecules are the angiogenic vascular endothelial growth factor (VEGF) and the anti-angiogenic protein pigment epithelium-derived factor (PEDF). All these devastating processes are focused on the macula, the place for central and sharp vision in the human retina.

Current Treatment

The state of the art of exudative AMD treatment makes use of anti-VEGF molecules (e.g. Ranibizumab-Lucentis®) which bind the VEGF protein. The intravitreal injection of anti-VEGF molecules stops the neovascularisation by disrupting the angiogenic cascade. Due to the short half-life of the molecules and the sustained intraocular VEGF protein expression, the therapy needs to be repeated monthly in average.

To avoid severe side effects, high costs on health care and the overall burden of therapy on the patients, an alternative therapeutic approach has been developed. The induction of increased intraocular PEDF levels will regenerate the homeostasis of angiogenic and anti-angiogenic molecules, counteract the increased VEGF expression and inhibit neovascularisation.

Therapeutical Approach of TargetAMD

The innovative therapeutic approach, realised by the interdisciplinary and international TargetAMD consortium, funded within the 7th Framework Program of the European Commission, comprises the subretinal transplantation of genetically modified, autologous iris pigment epithelial (IPE) cells.

Gene transfection with the recombinant PEDF will cause an overexpression of the protein providing a long-lasting cure for exudative AMD. Stable PEDF gene delivery will be based on the well-established non-viral hyperactive Sleeping Beauty (SB100X) transposon system, which combines the efficacy of viral delivery with the safety of naked DNA plasmids. This personalised approach, combining cell with gene therapy, will replace degenerated RPE cells, regenerate the neuroretinal environment, and offer a long-life therapeutic solution.

Raman Spectroscopy as Tool for Quality Control of the IPE Cells

Autologous cells undergo an electroporation step to be accessible for the PEDF gene. It is planned, that the cells are treated right after taking the biopsy and further-more are transplanted into the patient as fast as possible. However, there is currently no in-process quality control the transfection rate of the cells possible. The major limitations are the low cell count available for analysis (the whole process only treats about 5000-10000 cells) and the limited timeframe of about 1 h. It is possible to control the transfection rate with tools like Western Blot (2 days), ELISA (½ day), pPCR (½ day), CelltiterGlo Assay (½ day), microbiological cultures (2 weeks), image-based cytometry (1 h), or fluorescence microscopy (5 min). However, all these methods require cells that were cultured for at least 3 weeks before analysis and can only be used for in vitro experiments. These tests would suffice the requirements of a clinical study.

The Raman spectroscope-microscope system could be a suitable tool for the in-process control of the transfected cells in a GMP-controlled environment. The fast and non-invasive analysis of living cells would fulfil all of the most important requirements in this process.

The transfected and suspended cells can be selected visually in a standard bright field microscopy setup. After the visual control of the particle, the Raman measurement with a non-destructive laser can begin. Since the cells are suspended in a buffered solution, it is not possible to select specific cell compartments for analysis, so that in the end an averaged spectrum of the whole cell is generated. For statistical purposes, this analysis step is done for a multitude of cells so that the automated evaluation algorithms can estimate the proportion of successfully transfected cells.

Example 2

AMD Detection with Raman Spectroscopy

Raman Analyses of IPE Cells

Cell Preparation

In a first experiment, four samples have been examined:
1. hRPE Ko: control cells with electroporation treatment
2. hRPE pFAR-Venus: cells transfected with the pFAR-Venus plasmid
3. hRPE pFAR-PEDF: cells transfected with the pFAR-PEDF plasmid The first sample was measured to assess the influence of only electroporation on the cells. Samples 2 and 3 are each additionally transfected with a plasmid. pFAR-Venus is a reporter gene which is expressing a fluorescent protein, if it is correctly transfected into the cell. Subsequently, the amount of fluorescent cells in this sample can be used to estimate the transfection rate in the pFAR-PEDF samples. Finally, the pFAR-PEDF sample represents the final product which has to be controlled in a clinical application.

Two different batches of cells were analysed and differed mainly from each other because of the time spent in a cell culture. During cultivation, the cells tend to lose their pigmentation, which in turn also affects the Raman spectra.

For these measurements, all samples were fixed in 4% PFA for 5 min and subsequently washed multiple times with PBS.

Raman Measurement

All Raman spectra were acquired with a Raman spectroscope-microscope system which is equipped with a 785 nm laser and is set up as an inverted confocal Raman microscope. At the same time, the visual examination of the cells is possible with this device. For this experiments, 60-100 cells were measured per sample at 3 s integration time and 10 accumulations with 80 mW laser power and a 60× water-immersion objective (Olympus) corrected to 0.17 mm. All cell suspensions were put in an ibidi 8-well slide with Borosilicate glass bottom for measurement.

Data Processing

All spectra were processed automatically using standardised pre-processing algorithms developed by CellTool. The data underwent cropping to 500-1800 $cm^{-1}$, background removal using a partial-least squares algorithm (see Eilers, P. H. C. A, Anal. Chem. 75, 3631-3636 (2003), cosmic spike removal (see Schulze, H. G. & Turner, R. F. B., Appl. Spectrosc. 67, 457-462 (2013)), median filtering and finally an interpolation to whole wavenumbers. These methods were mainly introduced to ensure the comparability of the spectra.

The Principal Component Analysis (PCA) was used for exploratory statistical data analysis. For discrimination between transfected and un-transfected cells, a cut-off has been introduced. The cut-off was defined as the 95% confidence interval around the control samples. Cells that show a PC score that is outside this border are assumed to be differentiated from the control group. All algorithms and statistical and multivariate methods were implemented using the SciPy (see Jones E, Oliphant E, Peterson P, et al. SciPy: Open Source Scientific Tools for Python, 2001, http://www.scipy.org/[Online; accessed 2017, Jul., 4]) and Scikit-learn package (see Scikit-learn: Machine Learning in Python, Pedregosa et al., JMLR 12, pp. 2825-2830, 2011) in custom Python scripts.

Visual Assessment of the Samples

As can be derived from FIG. 1, all cells look quite similar to each other. The pigmentation of the cells can be clearly seen as black spots. Besides from usual fixation artefacts, it does not seem to be possible to discriminate the samples from just the cell morphology. On the other hand, it can clearly be seen that no microbiological contamination is present.

Figure 2:
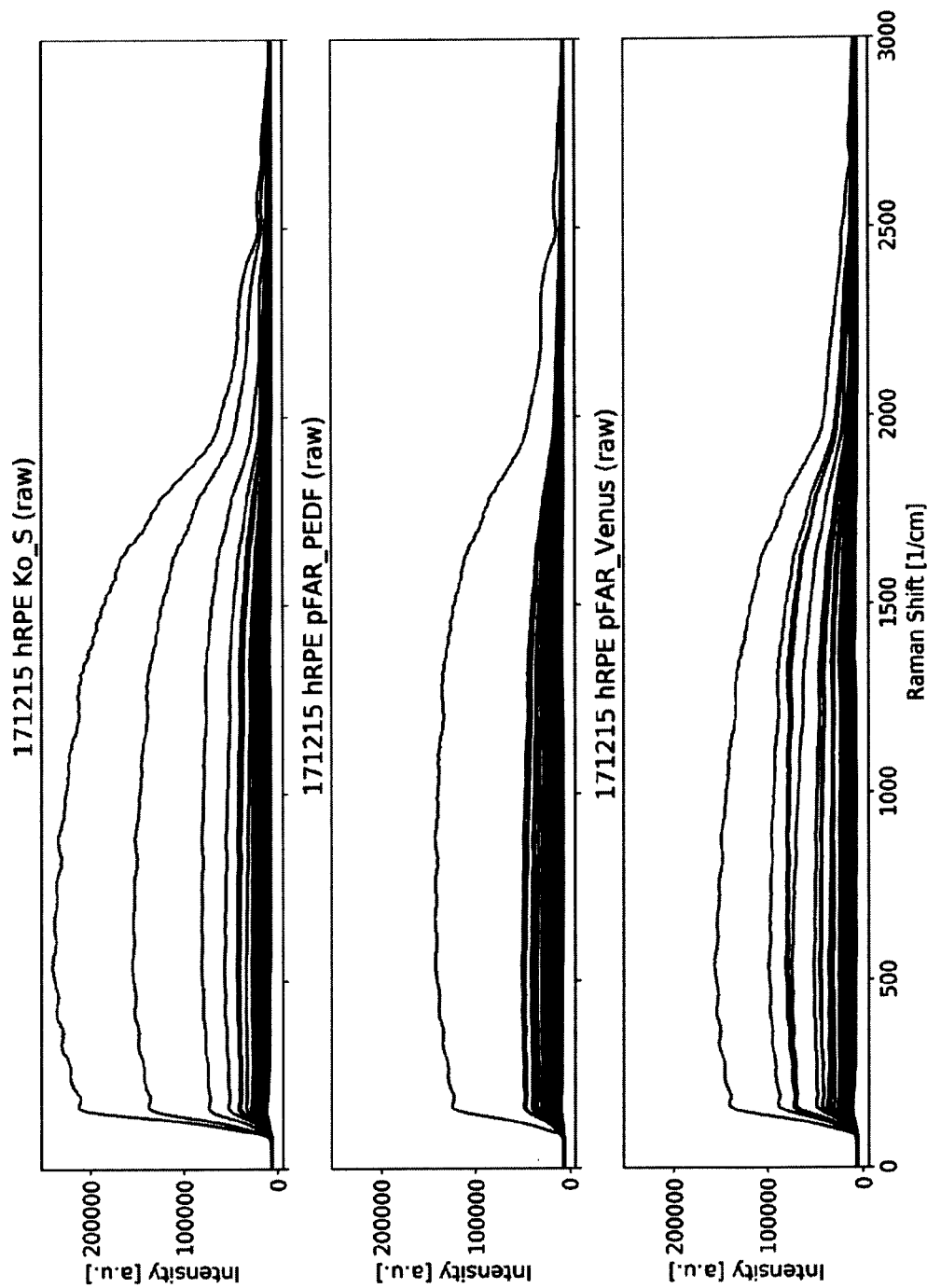
FIG. 2 shows overlay plots of the raw Raman spectra of a number of measured cells in one batch of samples. Each single thin line represents one Raman spectrum. The first subplot shows all Raman spectra of the control sample, the second subplot shows all spectra of the pFAR PEDF sample and the third subplot shows all spectra of the pFAR Venus sample. The few spectra containing a high overall intensity are affected strongly by fluorescence caused by cell pigmentation.
Figure 3:
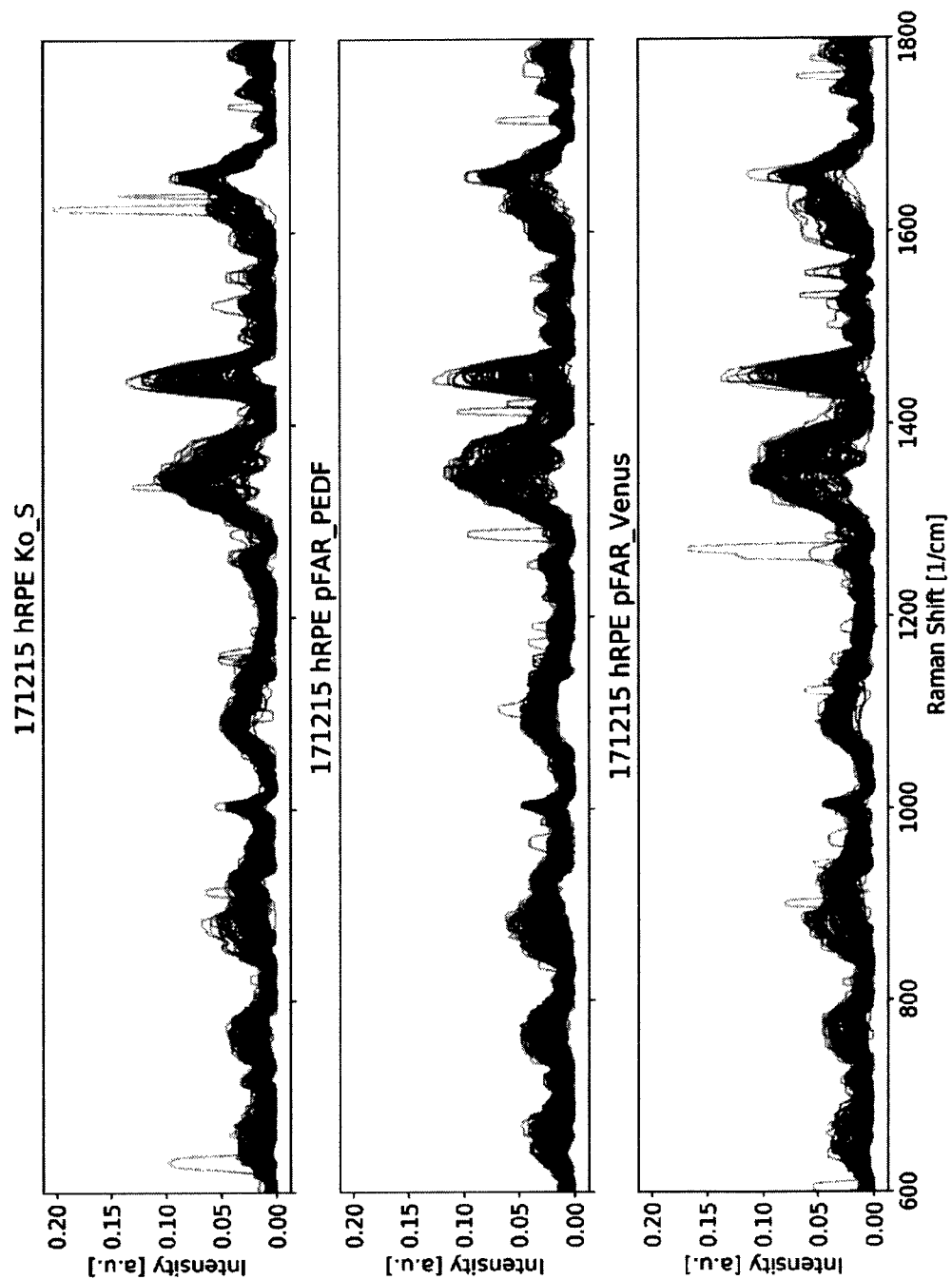
FIG. 3 shows overlay plots of the process Raman spectra of a number of measured cells in a batch of samples. Each single thin line represents one Raman spectrum. The first subplot shows all Raman spectra of the control sample, the second subplot shows all spectra of the pFAR PEDF sample and the third subplot shows all spectra of the pFAR Venus sample. The fluorescence could be largely reduced using mathematical and automated algorithms.
Figure 4:
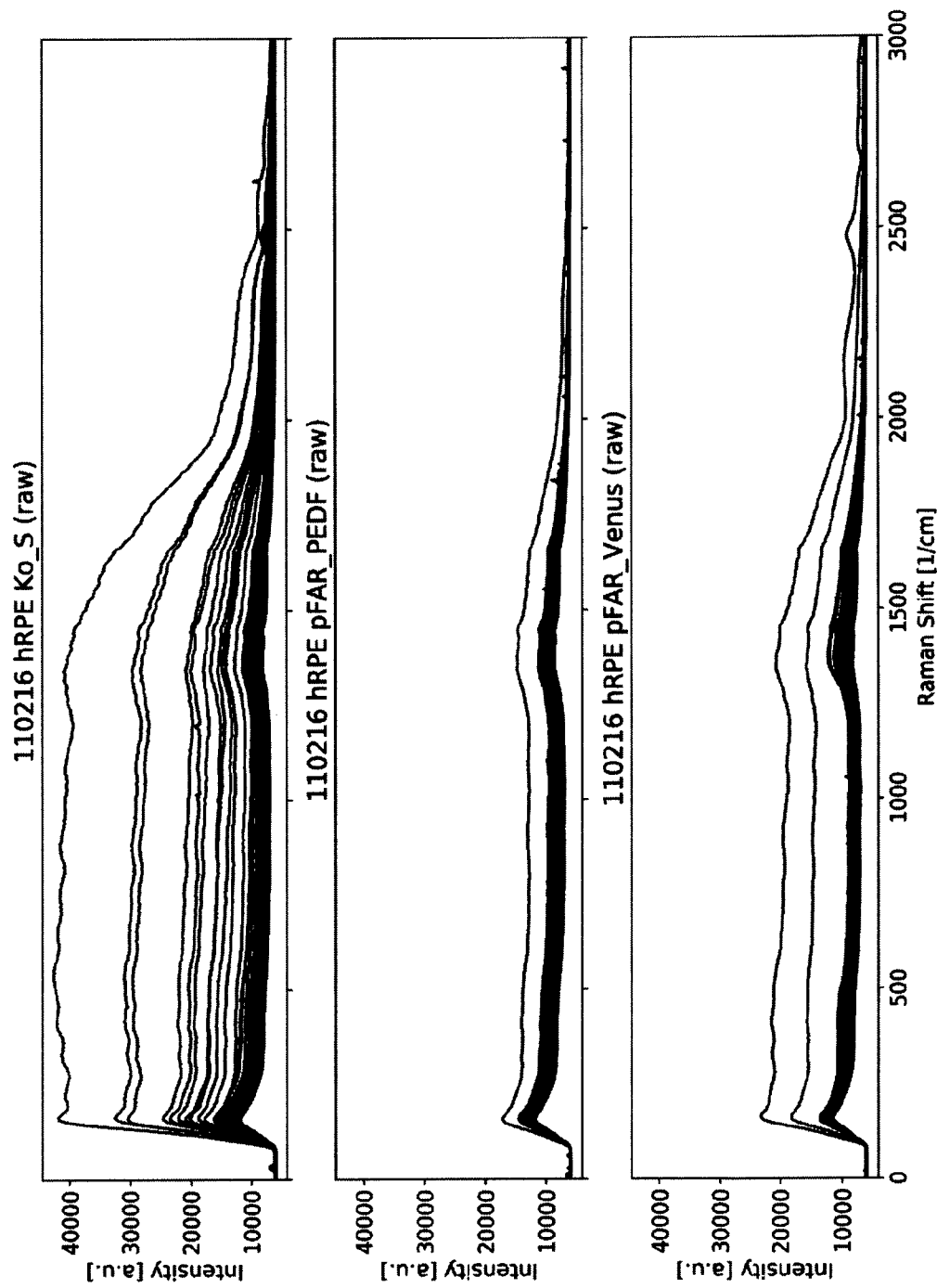
FIG. 4 shows overlay plots of the raw Raman spectra of a number of measured cells in a different batch of samples (in comparison to those depicted in FIG. 2). Each single thin line represents one Raman spectrum. The first subplot shows all Raman spectra of the control sample, the second subplot shows all spectra of the pFAR PEDF sample and the third subplot shows all spectra of the pFAR Venus sample. The few spectra containing a high overall intensity are affected strongly by fluorescence caused by cell pigmentation.
Figure 5:
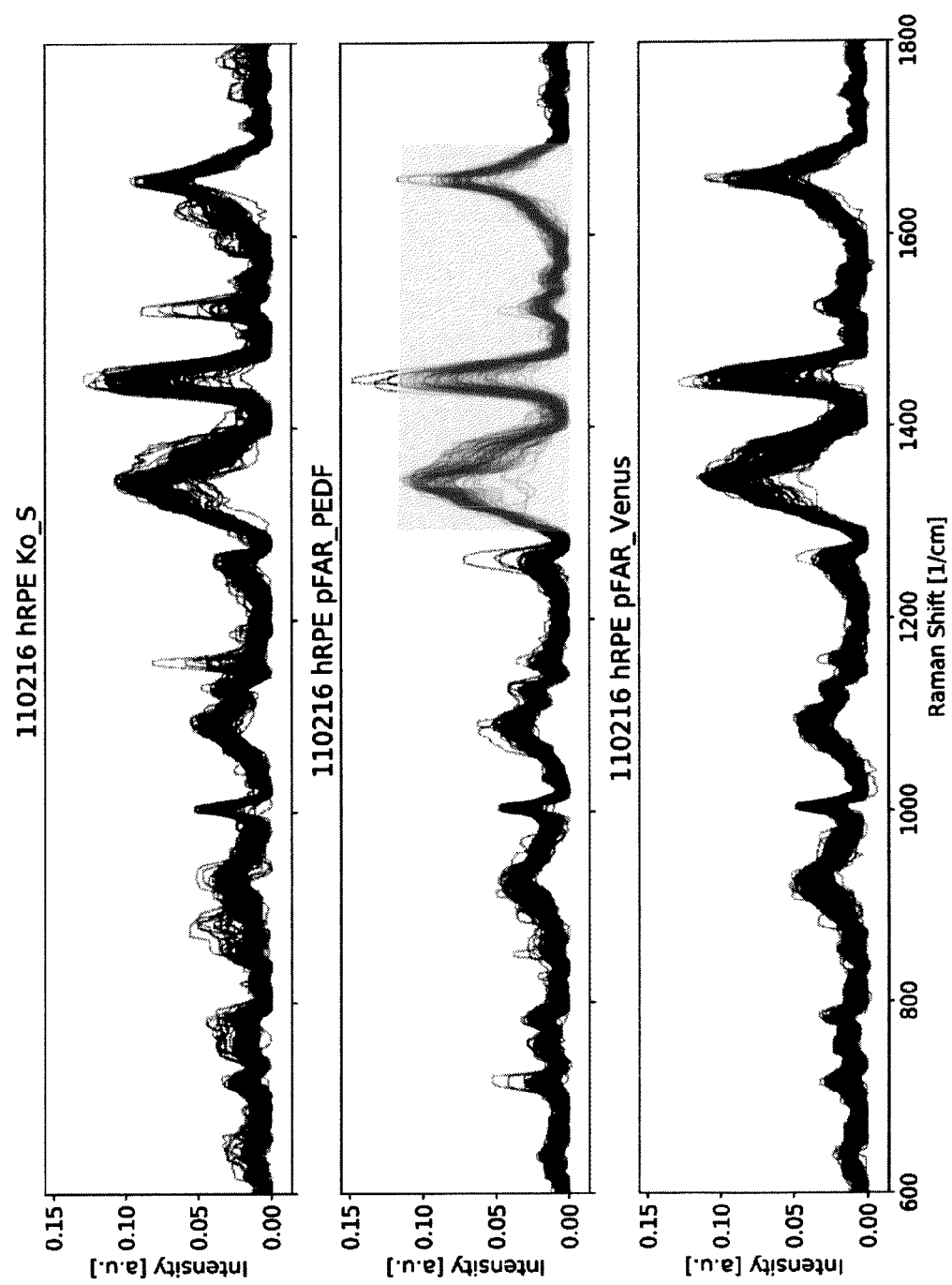
FIG. 5 shows overlay plots of the processed Raman spectra data of a number of measured cells in a different batch of samples (in comparison to those depicted in FIG. 3). Each single thin line represents one Raman spectrum. The first subplot shows all Raman spectra of the control sample, the second subplot shows all spectra of the pFAR PEDF sample and the third subplot shows all spectra of the pFAR Venus sample. The fluorescence could be largely reduced using mathematical and automated algorithms.

The raw Raman spectra partially show the large influence of the cell pigmentation as fluorescence (see FIGS. 2 and 4). The amount of pigmentation and therefore pigmentation does not seem to be constant over all samples. However, looking at the processed spectra of FIGS. 3 and 5, it seems that the background removal algorithms are quite effective, so that almost only Raman peaks remain.

Statistical Data Analysis

Figure 6:
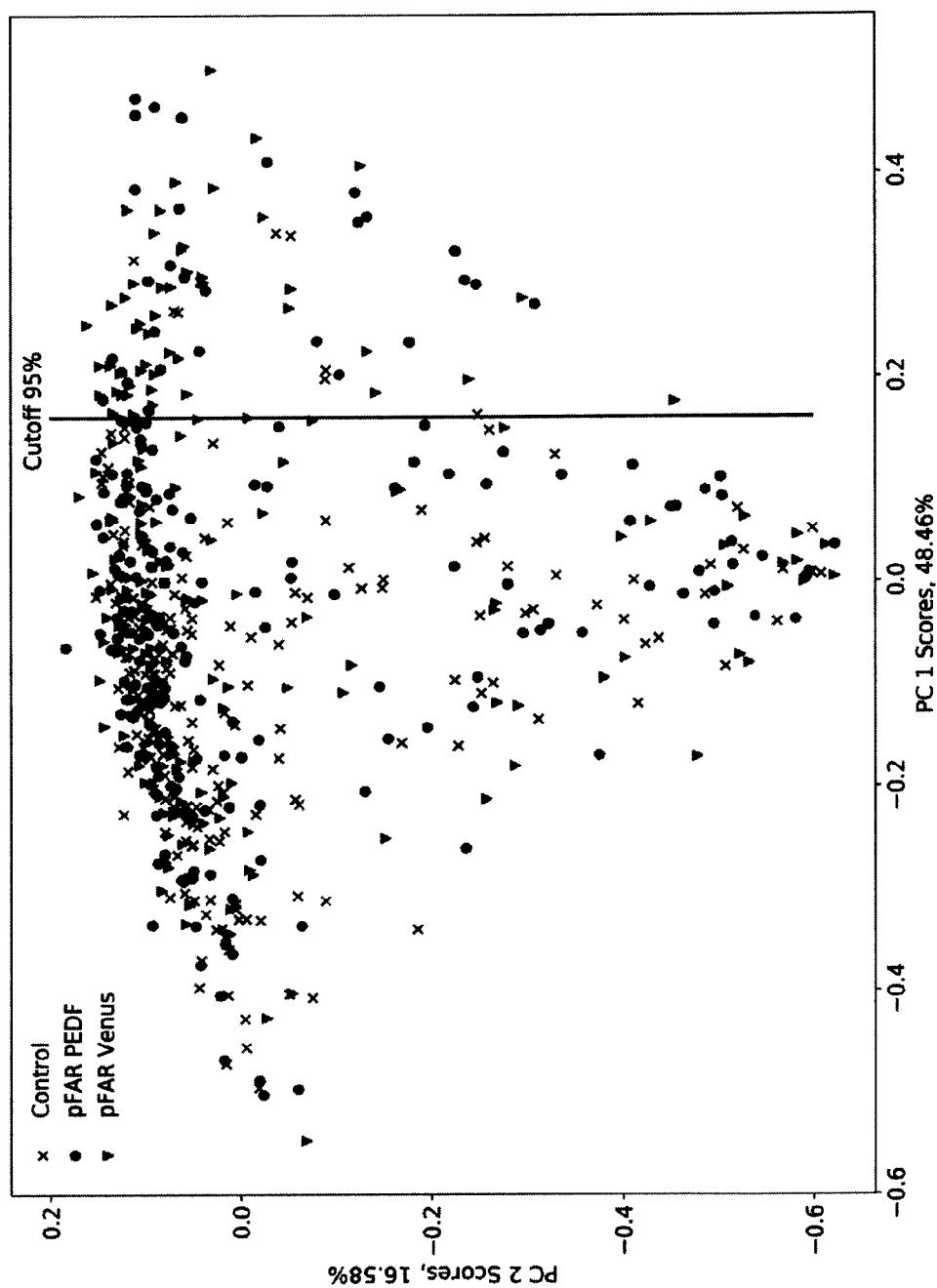
FIG. 6 depicts PCA scores plots of all the measured data. In the 2D scores plot a cutoff line is inserted at the 95% confidence interval of PC-1 of the control sample.
Figure 7:
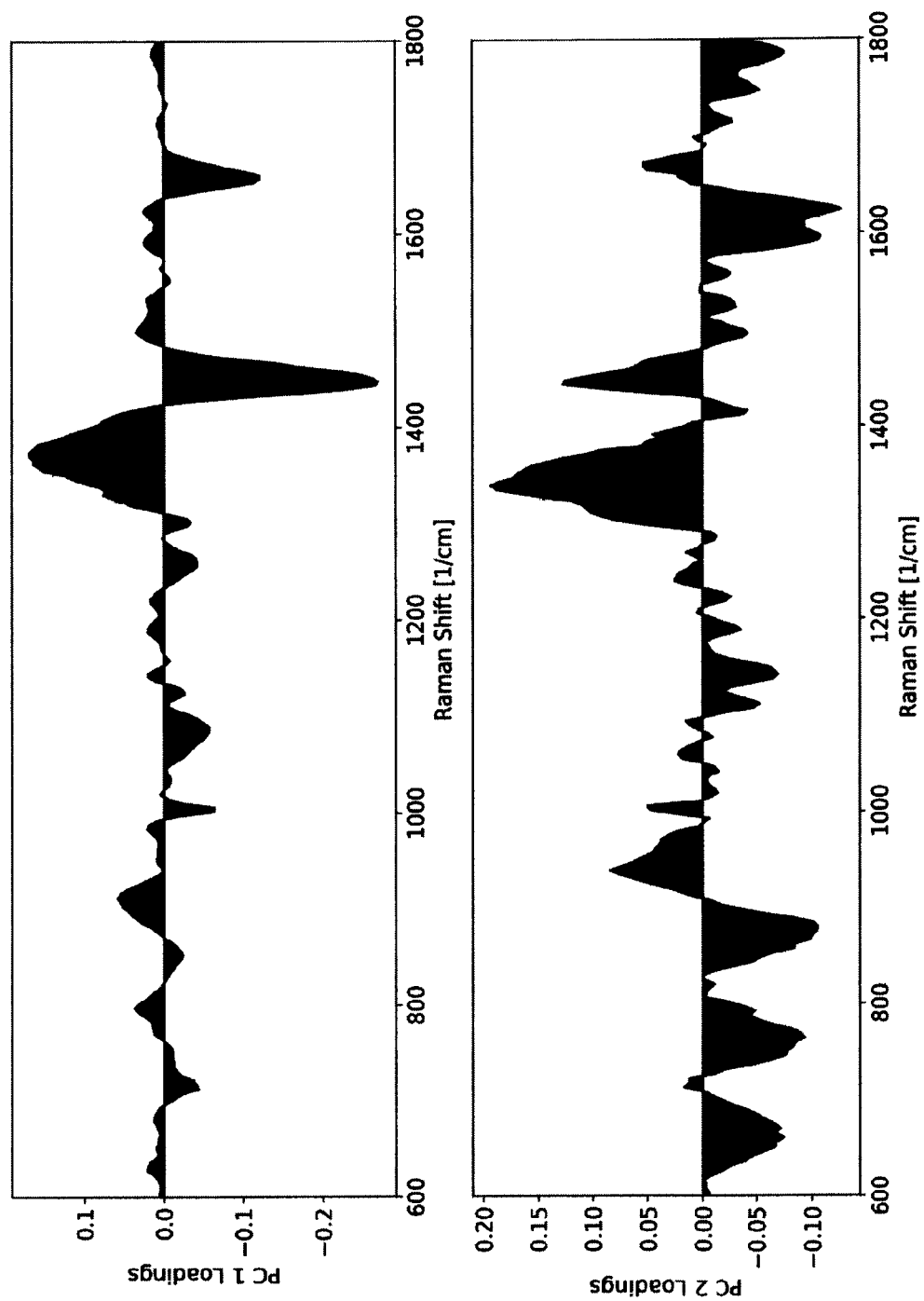
FIG. 7 depicts loadings plots of the first two principal components of all the measured data.

For the exploratory analysis of the data, the PCA is used as a visual tool. In FIG. 6 the PCA scores and Loadings are shown. PCA scores describe the relative position of every single Raman spectrum to all other analysed Raman spectra. The different PC-axes are mathematically orthogonal to each other, which means that the PC-values are independent from each other. The PCA loadings describe the relation of each PC score to its original Raman spectrum compared to the average of all other spectra. PCA scores of one point and the corresponding PCA loadings combined describe its original spectrum.

In the PCA scores plot, it can be seen that the transfected samples differ from the control samples on the PC-1 axis. Hence, the cut-off line at the 95% confidence interval of the control samples has been introduced. The PC-1 Loadings show that the peaks mainly responsible for this separation are at 1350 $cm^{-1}$, 1450 $cm^{-1}$ and 1650 $cm^{-1}$. However, the peak at 1350 $cm^{-1}$ is probably mainly a residual peak from the specimen holder. The other two peaks describe a CH deformation vibration and the Amide I Band in proteins respectively.

If this value at PC-1=0.1611 is taken, then 4.5% of the control samples, 15.5% of the pFAR PEDF samples, and 25.5% of the pFAR Venus samples have a significantly higher PC-1 score than the control groups. During fluorescence microscopy, the pFAR Venus transfection rate could be estimated to be around 35-40%.

Control samples and transfected samples show a high amount of similarities. However, there seems to be a significant amount of cells that do not match the control samples very well. Since the amount of outliers in the pFAR Venus samples and the fluorescence counting show similar results, it looks like Raman spectroscopy might be a valid tool for transfection detection.

The invention claimed is:

1. An in vitro method for determining a transfection efficiency of a cell, group of cells, or a live cell comprising:
   recording at least one Raman spectrum by means of Raman spectroscopy of said cell or group of cells;
   identifying a transfection of the cell or group of cells, wherein the transfection is a transfection of nucleic acids;
   conducting a statistical evaluation of the at least one Raman spectrum, wherein said nucleic acids are complexed or co-introduced with additional factors, the additional factors comprising proteins; and
   identifying by means of said statistical evaluation of the Raman spectrum the transfection of the cell or group of cells.

2. The method of claim 1, wherein said method for determination of the transfection efficiency is performed within a time period of about 5 min to about 60 min.

3. The method of claim 1 further comprising: recording said at least one Raman spectrum by an integrated Raman microscope-spectroscope system of said cell or group of cells.

4. The method of claim 3, additionally comprising a step of morphological determination of said cell or group of cells or morphological comparison between the cells or within said group of cells, or additionally comprising a step of fluorescently characterizing said cell or group of cells and/or a comparison between the cells or within said group of cells.

5. The method of claim 4, wherein said determination of transfection efficiency by recording at least one Raman spectrum is performed at a subsection of the cell, the subsection of the cell comprising the nucleus, the cytoplasm, the cell membrane area, the mitochondria, a vacuolic structure, or the microtubule organizing center (MTC).

6. The method of claim 1, additionally comprising the marking of a cell of interest under microscopic view with a virtual label to allow for visual tracking.

7. The method of claim 1, wherein conducting the statistical evaluation of the at least one Raman spectrum comprises a principal component analysis and/or a cluster analysis, wherein a predefined threshold value is used to differentiate between a transfected and a non-transfected cell.

8. The method of claim 1, wherein the evaluation of the Raman spectrum comprises a spectral analysis of the Raman spectrum.

9. The method of claim 8, wherein in order to quantitatively determine which proportion of the cells of said group of cells is subject to a transfection, a plurality of recorded Raman spectra are respectively subjected to the statistical analysis, the statistical analysis comprising a principal component analysis.

10. The method of claim 1, wherein the evaluation of the Raman spectrum comprises collecting and arresting one cell in an optical trap in order to record the Raman spectrum, the Raman spectrum comprising an optical trap produced by an excitation beam of a Raman spectroscopy system.

11. The method of claim 1, wherein said cell or group of cells to be determined is located in a microfluidic system or a microfluidic channel.

12. The method of claim 1, wherein said determination of transfection is performed computer-based in order to determine transfection automatically or semi-automatically.

13. The method of claim 1, wherein said method is for determining the transfection rate of a cell or a group of cells.

14. The method of claim 1, wherein the method comprises the additional step of separating transfected and non-transfected cells.

15. The method of claim 1, wherein said group of cells is a group of about 60 to about 500 cells.

16. A device for determining the transfection efficiency of a cell or group of cells, wherein the device comprises:
   a first unit comprising a microscope system configured to visualize and/or fluorescently characterize the cells;
   a second unit comprising a Raman spectroscopy system configured to record a Raman spectrum of a cell or group of cells; and
   a third unit comprising an evaluation module that is combined with the Raman spectroscopy system and is configured to determine by means of the recorded Raman spectrum whether a cell or group of cells has been transfected with a nucleic acid,
   wherein the evaluation module is configured to perform a statistical evaluation of the at least one Raman spectrum,
   wherein said nucleic acids are complexed or co-introduced with additional factors, the additional factors comprising proteins,
   wherein the evaluation module is configured to, by means of said statistical evaluation of the Raman spectrum, identify a transfection of a cell or group of cells, and
   wherein the first unit and the second unit are integrated.

17. The device for determining the transfection efficiency of claim 16, wherein said device comprises:
   as a forth unit (iv) a microfluidic component for semi-automated measurement and/or transporting and/or separating said cells which is coupled to the Raman spectroscopy system; or
   an optical trap, the optical trap comprising a beam of electromagnetic radiation configured to provide the optical trap.

18. The device for determining the transfection efficiency of claim 16, wherein said second unit is a second evaluation module for performing a cluster analysis and/or a principal component analysis, which is configured to identify transfection of a cell or group of cells.

19. The device for determining the transfection efficiency of claim 16, wherein said device is configured to perform the determination of transfection computer-based in order to determine transfection automatically or semi-automatically.

20. The device for determining the transfection efficiency of claim 16, wherein said device is configured to additionally perform the determination of cells by means of fluorescence microscopy or said device is configured to additionally perform the determination of morphology of said cells or group of cells and/or a morphological comparison of said group of cells.

21. The device for determining the transfection efficiency of claim 16, wherein said device is configured to determine the transfection by recording at least one Raman spectrum at a subsection of the cell, the subsection of the cell comprising the cytoplasm, the cell membrane area, the mitochondria, a vacuolic structure, or the microtubule organizing center (MTC).

* * * * *